United States Patent
Franssen et al.

(10) Patent No.: US 6,943,874 B2
(45) Date of Patent: Sep. 13, 2005

(54) APPARATUS FOR INSPECTING A SURFACE

(75) Inventors: Roger Franssen, Montzen-Plombières (BE); Hogo Uijtdebroeks, Hasselt (BE)

(73) Assignee: Centre de Recherches Metallurgiques, A.S.B.L., Brussels (BE)

( * ) Notice: Subject to any disclaimer, the term of this patent is extended or adjusted under 35 U.S.C. 154(b) by 276 days.

(21) Appl. No.: 10/221,668

(22) PCT Filed: Aug. 1, 2002

(86) PCT No.: PCT/BE02/00003

§ 371 (c)(1),
(2), (4) Date: Sep. 16, 2002

(87) PCT Pub. No.: WO02/055999

PCT Pub. Date: Jul. 18, 2002

(65) Prior Publication Data

US 2004/0021855 A1 Feb. 5, 2004

(30) Foreign Application Priority Data

Jan. 16, 2001 (BE) .......................... 2001/0034

(51) Int. Cl.$^7$ .............................................. G01N 21/88
(52) U.S. Cl. .............................. 356/237.1; 250/559.08; 164/480; 164/428; 164/4.1; 72/39; 356/600
(58) Field of Search .......................... 356/237.1, 237.2, 356/237.3, 600, 601; 164/428, 480, 4.1; 250/559.08, 239, 559.48; 72/39

(56) References Cited

U.S. PATENT DOCUMENTS 5,331,178 A  *  7/1994  Fukuda et al. ......... 250/559.08

FOREIGN PATENT DOCUMENTS

EP  0547227 A1  6/1993
EP  0697591 A1  2/1996

OTHER PUBLICATIONS

Patent Abstracts of Japan, vol. 9, No. 29, Feb. 7, 1985 & JP 59 174204 A (Nippon Kokan KK), Oct. 2, 1984.
Patent Abstracts of Japan, vol. 1996, No. 7, Jul. 31, 1996 & JP 08 068759 A (Kobe Steel Ltd.), Mar. 12, 1996.

* cited by examiner

Primary Examiner—Richard A. Rosenberger
Assistant Examiner—Vincent P. Barth
(74) Attorney, Agent, or Firm—Jacobson Holman PLLC

(57) ABSTRACT

The invention concerns an apparatus for inspecting a surface, in particular the surface of a mill roll, comprising a housing wherein are arranged means for transmitting and receiving a light beam, and an optical coupling device arranged on the outer surface of a front wall of the housing. The optical coupling device comprises: (a) a component (5), called fluid dispenser, (b) a hollow cylindrical nozzle (11), and (c) a mobile tubular component (16), successively traversed by the light beam. The mobile tubular component (18) is arranged partly inside the cylindrical nozzle (11), so as to be able to slide inside said cylindrical nozzle, and partly exits therefrom in the extension thereof, towards the surface to be inspected (2). Different cross-sections (shoulders 14, 19) are provided in the cylindrical nozzle (11) and in the mobile tubular component (16), in particular for limiting said sliding movement. The mobile tubular component (16) is positioned in the cylindrical nozzle by the sole effect of the coupling fluid pressure on its end surfaces. The device can further comprise means (21, 22) for preventing the rotation of the tubular component (16) about its longitudinal axis.

9 Claims, 2 Drawing Sheets

APPARATUS FOR INSPECTING A SURFACE

This is a nationalization of PCT/BE 02/00003 filed Aug. 1, 2002 and published in French.

TECHNICAL FIELD

The present invention relates to an apparatus for inspecting a surface, in particular but not exclusively, the surface of a working roll of a steel strip mill.

PRIOR ART

The prior art includes numerous applications where the condition of the surface of a production tool at least partially determines the quality of the manufactured product. One particular case of great importance is that of the production of steel strips, the surface finish of which depends to a large extend on the surface condition of the working rolls of the mill.

To clarify the ideas involved, the invention will be described here with reference to this particular application. However, it goes without saying that the invention per se is independent of this application and, instead, can advantageously be implemented in any situation involving comparable working conditions.

The surface condition of the mill rolls, such as the working rolls of the finishing cages of a strip rolling mill, has a major effect on the surface finish of the strips, which are intended for example for the production of automobile body sheets. During rolling, the surface of the rolls deteriorates due to the effect of the thermal and mechanical stresses to which it is subjected. This deterioration can be such that oxide films are torn away and may subsequently be found encrusted on the surface of the strip.

It is therefore important to inspect the surface of the rolls regularly in order to detect as soon as possible the defects that could compromise the quality of the rolled products.

Initially, inspection of the rolls consisted in a simple visual inspection carried out by an operator when replacing the roll. In certain cases, intermediate inspections were required, which then made it necessary to stop the rolling mill and sometimes even to remove the rolls. These intermediate stops are very time-consuming, thus entailing a loss of productivity. Moreover, the subjective nature of such a visual inspection can affect its quality. Consequently, it does not meet the current requirements of reliability, reproducibility and speed.

There are of course apparatuses that in principle allow this inspection to be carried out in a reliable and reproducible manner. However, their use is fraught with major practical difficulties due to the conditions prevailing near the mill rolls. In addition to a high temperature, conditions are particularly unfavourable there, owing to splashes of cooling water and lubricating oil which may occur near the inspection device and make any direct inspection impossible.

Devices referred to as optical coupling devices, which are intended to improve this inspection by targeting through a column of water created between the inspection apparatus and the surface to be inspected, have also already been proposed.

In general terms, the inspection apparatuses fitted with these known devices comprise, on the one hand, an emitter which sends a light beam towards the surface to be inspected and, on the other hand, a receiver, which catches the light beam reflected by this surface. The aim of the invention likewise falls within this category. In this regard, it should be understood that the light beam in question here includes both the incident beam emitted by the emitter and the reflected beam caught by the receiver. The optical coupling device must therefore allow both of these beams—the incident beam and the reflected beam—to pass through.

One important drawback of known optical coupling devices is that they are generally rather complicated, which does not make their manufacture or maintenance or, ultimately, their use any easier.

Consequently, there is a need for an optical coupling device that is simple and low-cost and allows to carry out the inspection of a surface, such as the surface of a mill roll, within good conditions.

PRESENTATION OF THE INVENTION

The present invention aims to respond to this need. As characterised in the claims, the invention relates to an apparatus for inspecting a surface with a simple optical coupling device which guarantees a perfect view of the surface to be inspected, avoiding disturbances of the visual field by substances such as splashing water or oil.

In accordance with the invention, an apparatus for inspecting a surface, in particular the surface of a mill roll, which comprises a housing, in which means for emitting and receiving a light beam are arranged, in which the front wall of said housing, i.e. the wall turned towards the surface to be inspected, has a transparent window to allow said light beam to pass between said emission and reception means and the surface to be inspected, and in which an optical coupling device is arranged on the outer face of said front wall of the housing in such a way that its optical axis is at least substantially parallel with the axis of said light beam, is characterised in that:

a. said optical coupling device comprises:
   a component, referred to as fluid dispenser, fixed to said front wall of the housing and pierced by an opening to allow said light beam to pass through;
   a hollow cylindrical nozzle arranged as an extension of said opening to allow said light beam to pass through;
   a mobile tubular component arranged partially within said cylindrical nozzle, as an extension of the latter, and which can slide within said cylindrical nozzle;
b. the fluid dispenser is provided with an inlet orifice for the coupling fluid and with passages connecting said inlet orifice to said opening;
c. the hollow cylindrical nozzle is leaktightly assembled with the fluid dispenser;
d. the hollow cylindrical nozzle has a constant inner section over most of its length and an outlet portion, the section of which is smaller than said inner section, an internal shoulder thus being formed near the outlet of said cylindrical nozzle;
e. said mobile tubular component has a head, the section of which is slightly smaller than the inner section of said cylindrical nozzle, and an elongated portion, the section of which is slightly smaller than the section of said outlet portion of the cylindrical nozzle, the head and the elongated portion of said tubular component being connected by an external shoulder;
f. said tubular component is inserted into said cylindrical nozzle in such a way that said elongated portion projects from said outlet portion and that the external shoulder of said tubular component cooperates with said internal shoulder of said cylindrical nozzle.

The opening for the passage of the light beam provided in the fluid dispenser is advantageously smaller than the section of the head of the mobile tubular component. The fluid dispenser thus forms a stop that limits the movement of the mobile tubular component in the direction of said front face of the housing.

According to a particular characteristic, the cylindrical nozzle has, at the level of said internal shoulder, passages establishing the communication between the inner space of the cylindrical nozzle and the outside.

According to another advantageous characteristic, said mobile tubular component has an inner section, which is smaller in its end region on the same side as the head than in its elongated portion. This reduction in the inner section leads to an increase in the surface of the end face on the same side as the head and consequently also to an increase in the force exerted on this surface by the pressure of the water in the direction of the surface to be inspected.

At least in its end region which can come into contact with the surface to be inspected, the mobile tubular component is advantageously made from a material whose hardness is less than that of the surface to be inspected. From the time when it is put into service, the end of the mobile tubular component can thus progressively wear away on contact with the roll so as to adapt to the curvature of the roll. When a roll is changed, however, this tubular component may turn about its axis, entailing a coupling defect, which then only gradually disappears.

According to yet another advantageous characteristic, said mobile tubular component can therefore be provided with means preventing its rotation about its longitudinal axis. In particular, these means can comprise a pin, provided on the inner surface of the outlet portion of the cylindrical nozzle, and a longitudinal groove, arranged in the outer lateral surface of the elongated portion of said mobile tubular component, and in which said pin is engaged.

In the device according to the invention, said tubular component has end faces in the form of correspondingly shaped crowns, the respective sizes of which are determined by the respective inner and outer sections of the two ends of the component. That being so, the optical coupling fluid can act on these two surfaces and thus make the tubular component slide within the cylindrical nozzle so as to automatically position it in an optimum manner with respect to the surface to be inspected.

An essential advantage of the device according to the invention is that the tubular component is positioned, possibly even in contact with the surface to be inspected, solely by the action of the optical coupling fluid.

The expression "constant inner section" should be understood to mean that the inner section of the cylindrical nozzle has the same shape and the same dimensions over the entire length concerned. In the case of a circular section, this means that the inner diameter of the cylindrical nozzle remains constant over this length. In the same way, the outer section and the inner section of a component respectively relate to the section defined by the outer contour and the inner contour of this component, respectively.

Additional details and advantages will emerge from the detailed description of exemplary embodiments illustrated in the attached drawings, which are not to any particular scale.

In these drawings, only the elements essential for a proper understanding of the invention have been shown. Moreover, identical or similar elements are designated by the same reference numerals in the various figures. For the sake of clarity in the following description, which is given by way of a simple exemplary embodiment, the optical axis of the coupling device coincides with the axis of the light beam and the components of the coupling device are rotationally symmetrical about this axis.

EMBODIMENTS OF THE INVENTION

Figure 1:
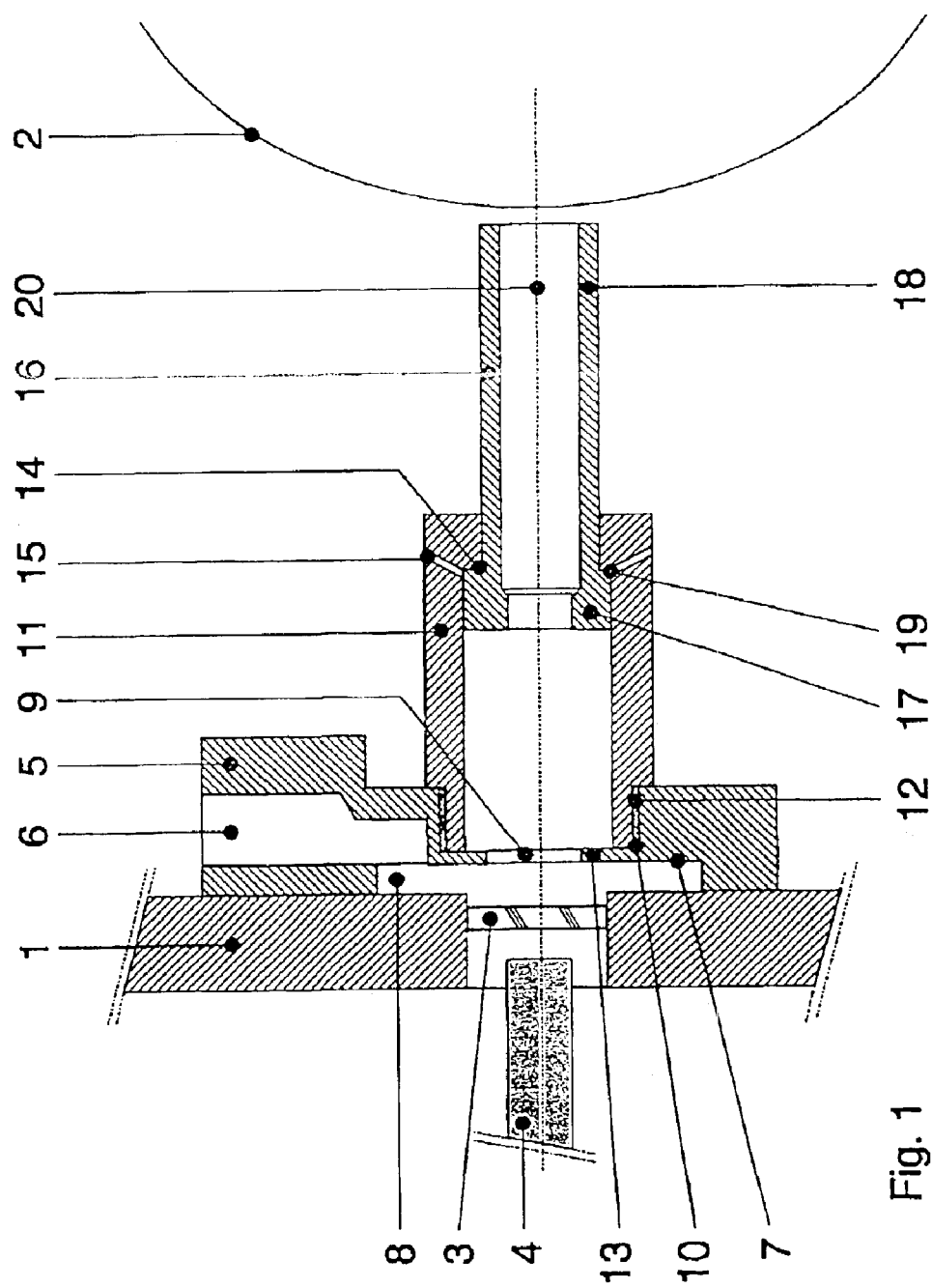
FIG. 1 shows a longitudinal section through an optical coupling device according to the invention mounted on a housing of an apparatus for inspecting the surface of a mill roll.

FIG. 1 shows an optical coupling device mounted on a housing 1 illustrated indicatively by a portion of its front wall, which is turned towards the surface of a mill roll 2 to be inspected.

Without going into detail here, it may be stated more specifically that this front wall 1 comprises a transparent leaktight window 3, through which can pass a light beam, symbolised by its axis, coming for example from an assembly 4 containing a light source forming the light beam emitted towards the mill roll 2 to be inspected and an optical receiving device, which catches the light beam reflected by the surface of the roll 2.

A component 5, referred to here as water dispenser, is fixed to this front wall 1 and has a lateral water inlet orifice 6. A recess 7 is arranged at the rear of said component 5 and, together with the wall 1, delimits a space 8 extending opposite the window 3. This space 8 communicates with the inlet orifice 6. Opposite the window 3, the component 5 is also pierced by an opening 9 communicating with said space 8 and extended along the axis of the light beam by an internally threaded core print 10 of a larger diameter.

At a first end, a cylindrical nozzle 11 has an externally threaded core print 12, which is screwed into the component 5 until it abuts a shoulder 13 formed by the component 5. At its other end, the cylindrical nozzle 11 has a reduction in section with an internal annular shoulder 14. Passages 15 leading towards the exterior of the cylindrical nozzle open into the angle of said shoulder 14.

A mobile tubular component 16 is arranged inside of the cylindrical nozzle 11 and has an end portion or head 17 housed within the cylindrical nozzle 11 and an elongated portion 18 emerging from the latter with its narrow end. The outside diameter of the elongated portion 18 is smaller than that of the head 17; the mobile tubular component 16 thus has an external annular shoulder 19 co-operating with the internal annular shoulder 14 of the cylindrical nozzle. Moreover, the opening 9 made in the component 5 has a smaller diameter than the outside diameter of the head 17 and thus radially extends the shoulder 13 mentioned above. The shoulder 13 thus likewise serves as a stop for the mobile tubular component 16; in this way, the latter is prevented from passing through the opening 9 and penetrating into the space 8, where it could interfere with the proper functioning of the device, in particular the circulation of the coupling fluid.

It goes without saying that the mobile tubular component 16 should be inserted into the cylindrical nozzle 11 before the latter is screwed onto the component 5. It will furthermore be understood that the opening 9, the cylindrical nozzle 11 and the mobile tubular component 16 are coaxially aligned with the axis 20 of the light beam.

Figure 2:
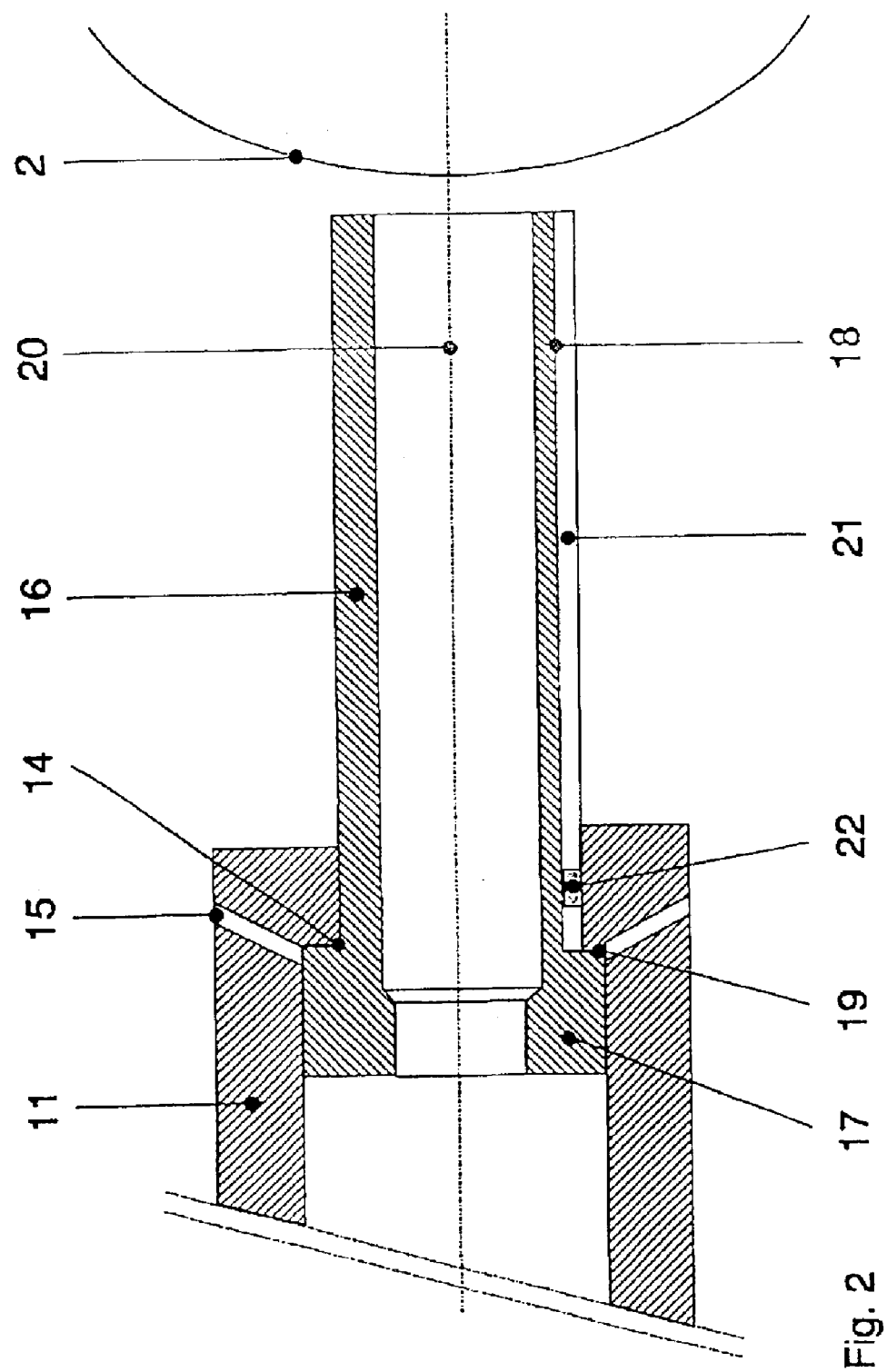
FIG. 2 shows an enlarged detail of the device of FIG. 1 provided with means preventing the rotation of the mobile tubular component.

FIG. 2 shows an enlarged detail of the device in FIG. 1, according to which the mobile tubular component 16 is provided with an external longitudinal groove 21, in which a lock pin 22, provided in the outlet region of the cylindrical nozzle 11, engages. The mobile tubular component 16 can thus longitudinally slide in the cylindrical nozzle while being prevented from turning about its longitudinal axis.

This optical coupling device functions as follows:

The water introduced via the inlet orifice 6 passes into the space 8, where it is distributed over the entire surface of the window 3. Via the opening 9, it next flows into the cylindrical nozzle 11, then into the mobile tubular component 16 and, finally, escapes via the space between the mobile tubular component 16 and the surface of the roll 2.

Under the effect of the pressure of the water passing from the cylindrical nozzle 11 into the mobile tubular component 16, the latter is pushed in the direction of the surface of the roll 2. A column of water protected by the mobile tubular component is thus created and the length of the latter automatically adapts to the distance separating the window 3 from the surface of the roll 2. However, this situation implies that the mobile tubular component comes into contact with the surface of the roll. In reality, the coupling water escaping between the surface of the roll 2 and the mobile tubular component 16 exerts a counter-pressure on the end face of the latter, which pushes the mobile tubular component 16 back in the direction of the window 3. The mobile tubular component stabilises when the two pressures balance. The spacing thus obtained between the mobile tubular component and the surface of the roll, and hence the positioning of the mobile tubular component, can be regulated simply by changing the flow rate of coupling water.

In normal operation, the mobile tubular component 16 does not, in principle, touch the surface of the roll 2, which greatly reduces the risks of deterioration both of the mobile tubular component 16 and the surface of the roll 2. Nevertheless, when a roll is being changed, the mobile tubular component 16 may turn about its axis 20, with the disadvantages indicated above. The longitudinal groove 21 co-operating with the pin 22 prevents this rotation.

The optical coupling device according to the invention is not limited to the description above or to the illustration of it in the attached drawings. In particular, the invention likewise encompasses variants in which the various components of the device, namely the opening 9, the cylindrical nozzle 11 and the mobile tubular component 16, are not coaxially arranged with respect to the light beam 20. Moreover, the cross section of these components is not necessarily circular or in the form of an annular ring, respectively; on the contrary, it can have any other shape, in particular polygonal or elliptical, so as to define the position of the mobile tubular component and prevent its rotation, for example.

What is claimed is:

1. An apparatus for inspecting a surface, said apparatus comprising a housing, in which means for emitting and receiving a light beam are arranged, having a front wall turned towards the surface with a transparent window on the front wall to allow said light beam to pass between said emitting and receiving means and the surface, and having an optical coupling device arranged on the outer surface of said wall so that its optical axis is essentially parallel to the axis of said light beam, wherein said optical coupling device comprises:

a fluid dispenser component fixed to said wall and pierced with an opening to allow said light beam to pass through;

a hollow cylindrical nozzle leaktightly assembled with said fluid dispenser component and arranged as an extension of said opening, said fluid dispenser component being provided with an inlet orifice for a coupling fluid and with passages connecting said inlet orifice to said opening;

a mobile tubular component, arranged partially within said cylindrical nozzle, as an extension of the latter, and capable of sliding within said hollow cylindrical nozzle;

the hollow cylindrical nozzle having a uniform first inner diameter over most of its length and a second inner diameter over an outlet portion, said second inner diameter being smaller than said first inner diameter to form an internal shoulder near the outlet of said hollow cylindrical nozzle;

said mobile tubular component having a head with a first external diameter slightly smaller than said first inner diameter of said cylindrical nozzle, and an elongated portion with a second external diameter slightly smaller than the second inner diameter of said outlet portion of the cylindrical nozzle to form an external shoulder of said tubular component;

said elongated portion of the mobile tubular component being inserted into and projecting out of said outlet portion of the cylindrical nozzle and the external shoulder cooperating with said internal shoulder to stop the movement of said mobile tubular component in said hollow cylindrical nozzle.

2. The apparatus according to claim 1, wherein the diameter of the opening is smaller than the external diameter of the head of the mobile tubular component.

3. The apparatus according to claim 1, wherein said mobile tubular component has a smaller inner diameter in its end region on the same side as the head than in its elongated portion.

4. The apparatus according to claim 1, wherein said cylindrical nozzle and said mobile tubular component are each provided with means cooperating with each other to prevent rotation of said mobile tubular component about its longitudinal axis relative to said cylindrical nozzle.

5. The apparatus according to claim 4, wherein said means comprise a longitudinal groove, arranged in the outer lateral surface of the elongated portion of the mobile tubular component, and a pin provided in the outlet portion of the cylindrical nozzle and capable of engaging in said longitudinal groove.

6. The apparatus according to claim 1, wherein, at least in its end region, the mobile tubular component is made from a material whose hardness is less than that of the surface to be inspected.

7. The apparatus according to claim 1, wherein the optical axis of at least one of the components of the optical coupling device, namely the passage opening, the cylindrical nozzle and the mobile tubular component, coincides with the axis of said light beam.

8. The apparatus according to claim 7, characterised in that at least one of said components of the optical coupling device is rotationally symmetrical about said axis of the light beam.

9. An apparatus according to claim 1, wherein the surface to be inspected is the surface of a mill roll.

* * * * *